(12) United States Patent
Burken

(10) Patent No.: US 8,286,511 B2
(45) Date of Patent: Oct. 16, 2012

(54) ASSEMBLIES FOR USE IN EVALUATING SUBSURFACE CONTAMINATION, AND RELATED METHODS

(75) Inventor: Joel G. Burken, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 546 days.

(21) Appl. No.: 12/463,163

(22) Filed: May 8, 2009

(65) Prior Publication Data

US 2009/0277283 A1 Nov. 12, 2009

Related U.S. Application Data

(60) Provisional application No. 61/051,738, filed on May 9, 2008.

(51) Int. Cl.
*G01N 1/02* (2006.01)
(52) U.S. Cl. ................... 73/863.21; 73/864.44
(58) Field of Classification Search .............. 73/863, 73/863.21, 863.71, 863.81, 864, 864.43, 73/864.44
See application file for complete search history.

(56) References Cited

U.S. PATENT DOCUMENTS 4,549,612 A * 10/1985 Cushing ................ 175/20
5,263,359 A * 11/1993 Mookherjee et al. ........ 73/23.34

OTHER PUBLICATIONS

Lord et al., In vivo study of triazine herbicides in plants by SPME, The Royal Society of Chemistry, 129, pp. 107-108 (2004).
Lord, Solid Phase Microextraction Probe for In Vivo Pharmacokinetic Study, http://www.science.uwaterloo.ca/chemistry/pawliszyn/Research/invivospme.htm, 3 pages, May 8, 2009.
Ma, X. and J.G. Burken, VOCs Fate and Partitioning in Vegetation: Use of Tree Cores in Groundwater Analysis; *Environmental Science and Technology*, 36 (21) 4663-4668 (2002).
Ma, X. and J.G. Burken, Modeling of TCE Diffusion to the Atmosphere and Distribution in Plant Stems; *Environmental Science and Technology*, 39 (17), 4580-4586 (2004).
Schumacher, J.G., G.C. Struckhoff, and J.G. Burken, Assessment of Subsurface Chlorinated Solvent Contamination Using Tree Cores at the Front Street Site and Former Dry Cleaning Facility at the Riverfront Superfund Site, New Haven Missouri, 1999-2003, U.S. Geological Survey Scientific Investigations Report 2004-5049, 35 pages (2004).
Struckhoff, G., J.G. Burken, and J.G. Schumacher, Vapor-Phase Exchange of Perchloroethene between Soil and Plants; *Environmental Science and Technology*, 39 (6) 1563-1568 (2005).

(Continued)

*Primary Examiner* — Eric S McCall
(74) *Attorney, Agent, or Firm* — Harness, Dickey & Pierce, P.L.C.

(57) ABSTRACT

A method is provided for determining the presence and/or concentration of at least one contaminant in a subsurface at a test site. The method generally includes inserting a sampling assembly into at least one tree at the test site, processing at least part of the sampling assembly to determine if a contaminant is present in the at least one tree, and then correlating the presence and/or concentration of the contaminant in the at least one tree to presence and/or concentration of the contaminant in the subsurface. The sampling assembly is operable to sorb at least one contaminant located within the at least one tree to at least part of the sampling assembly. The sampling assembly may include a solid phase microextraction (SPME) sampling assembly having a SPME sampling device and a support configured to help position the SPME sampling device within a tree for sampling operation.

18 Claims, 14 Drawing Sheets

OTHER PUBLICATIONS

Vroblesky, D.A., User's guide to the collection and analysis of tree cores to assess the distribution of subsurface volatile organic compounds: U.S. Geological Survey Scientific Investigations Report 2008-5088, 59 pages (2008).

Ma, Xingmao and Joel G. Burken, TCE Diffusion to the Atmosphere in Phytoremediation Applications; *Environmental Science and Technology*, 37 (11), 2534-2539, (2003).

Loi et al., Solid-Phase Microextraction Method for In Vivo Measurement of Allelochemical Uptake; J. Chem. Ecol. 34:70-75 (2008).

W.L. Gore & Associates, Inc., Geochemical Services, GORE™ Modules for Passive Soil Gas Collection; http://www.gore.com/en_xx/products/geochemical/petroleum/surveys_petroleum_. . . , 1 page, May 20, 2010.

Burken, Joel G., Ph.D., Presentation: Vegetative Sampling for Plume Delineation and Site Monitoring; AEESP Conference, The University of Iowa, College of Engineering, Grand Challenges in Environmental Engineering and Science: Research and Education, 27 pages, Jul. 29, 2009.

Burken, Joel G., Ph.D., Presentation: Bioengineering Impacts on Organic Contaminant Rhizodegradation; BioEco (China), 26 pages, Jun. 2007.

Burken, Joel G., Ph.D., Presentation: Phytoremediation of VOC's: Understanding Fat & Innovative Applications; Academey of Forrestery (China), 38 pages, Oct. 23, 2006.

Sheehan, Emily Moore; Time-Weighted Average Solid-Phase Microextraction (TWA-SPME) for In-Planta Detection of Chlorinated Solvents, A Thesis, Missouri University of Science and Technology, 76 pages, 2009.

Waltermire, Kendra Marie; Comparison of In-Planta Sampling methods for Delineating Groundwater Contaminants, A Thesis, Missouri University of Science and Technology, 55 pages, 2009.

Vroblesky, D.A., User's guide to the collection and analysis of tree cores to assess the distribution of subsurface volatile organic compounds, U.S. Geological Survey Scientific Investigations Report 2008-5088, 74 pages (Jul. 2008).

Morrison, G.C. et al., Gas-phase exposure history derived from material-phase concentration profiles, ScienceDirect, Atmospheric Environment 41, (pp. 3276-3286) 11 pages (May 2007).

* cited by examiner

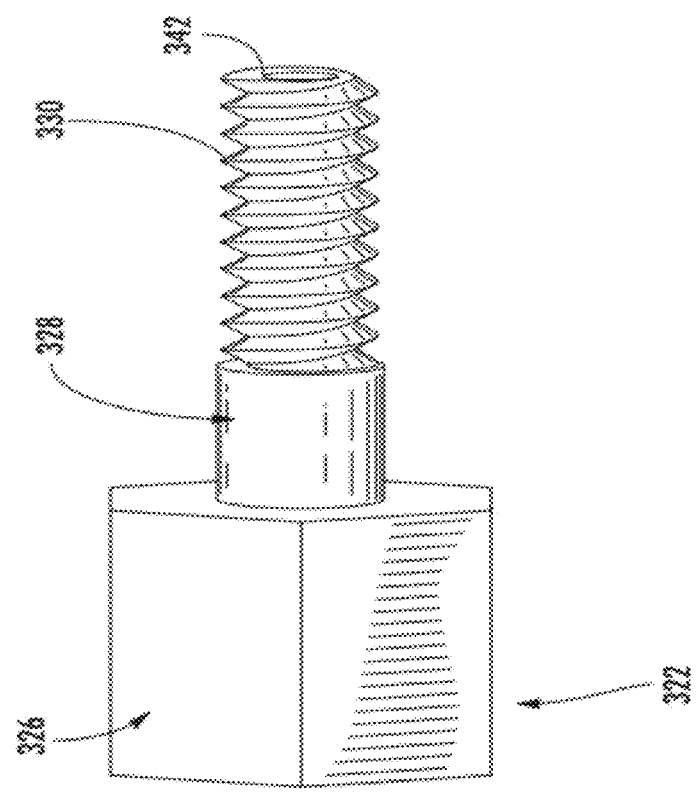
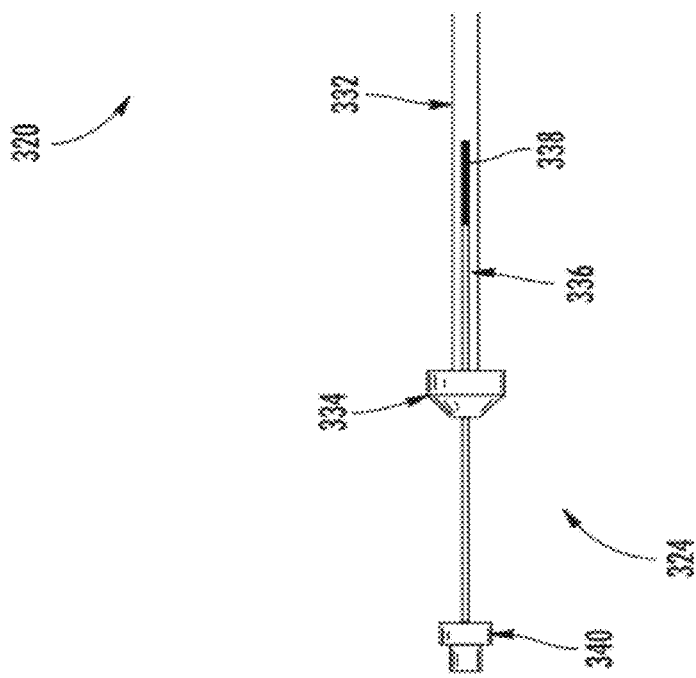
FIG. 4

ASSEMBLIES FOR USE IN EVALUATING SUBSURFACE CONTAMINATION, AND RELATED METHODS

CROSS-REFERENCE TO RELATED APPLICATION

This application claims the benefit of U.S. Provisional Application No. 61/051,738, filed May 9, 2008, the entire disclosure of which is incorporated herein by reference.

FIELD

The present disclosure relates generally to evaluating subsurface contamination, and more particularly to assemblies that can be used, for example, with in-planta analysis to help evaluate subsurface contamination, and related methods.

BACKGROUND

This section provides background information related to the present disclosure which is not necessarily prior art.

Plants (e.g., trees, vegetation at a site, etc.) are often used to treat, remediate, etc. contaminated soils, waters, etc. by making use of interactions between the plants and subsurface contaminants. For example, through phytoremediation, contaminants may be taken up into the plants and subsequently degraded (e.g., by microorganisms in the rhizosphere of the vegetation, by biomass of the vegetation, etc.), stored in biomass of the vegetation, released into the air (e.g., by transpiration through leaves, stems, etc.), etc.

Solid phase microextraction (SPME) is a sample preparation technique used for chemical analysis. FIG. 1 illustrates a typical SPME sampling device 1 configured to make use of the SPME sample preparation technique. The illustrated SPME sampling device 1 includes a fiber 3 (having a polymer coating 5) enclosed within a needle housing 7, and a plunger 9 connected to the fiber 3. The plunger 9 may be moved inwardly and/or outwardly of the needle housing 7 to correspondingly move the fiber 3 as desired.

Fibers of SPME sampling devices are coated with polymers having high sorption capacities that, when exposed to compounds of specific chemical natures, allow the compounds to sorb to the polymers proportionately to the concentration of the compounds in the surrounding environment. Following sorption, the fibers can, for example, be directly inserted into a gas chromatograph for desorption and analysis.

SUMMARY

This section provides a general summary of the disclosure, and is not a comprehensive disclosure of its full scope or all of its features.

Example embodiments of the present disclosure relate generally to methods for determining the presence of at least one contaminant in plants, such as a trees, or in other environmental media located at test sites. In one example embodiment, a method generally includes inserting a sampling assembly into a plant or other environmental media at a test site, and processing at least part of the sampling assembly to determine if a contaminant is present in the plant or other environmental media. The sampling assembly is operable to sorb at least one contaminant located within the plant or other environmental media to at least part of the sampling assembly.

Example embodiments of the present disclosure also generally relate to methods for determining the presence of at least one environmental contaminant in subsurface portions of test sites. In one example embodiment, a method generally includes creating a bore opening in multiple trees at a test site, inserting a sorption-based sampling assembly into the bore opening of each tree, processing at least part of each sampling assembly to determine if an environmental contaminant is present in the tree in which the processed sampling assembly is inserted, and correlating an environmental contaminant present in each tree to a subsurface below said tree. The sampling assembly is operable to sorb at least one environmental contaminant located within the tree in which the sampling assembly is inserted to at least part of the sampling assembly. And, the presence of the environmental contaminant in the tree is indicative of the presence of the environmental contaminant in the subsurface below said tree.

Other example embodiments of the present disclosure generally relate to sampling assemblies for collecting samples from trees at test sites. In one example embodiment, a sorption-based sampling assembly generally includes a body and a silicon tubing disposed generally over the body.

Still other example embodiments of the present disclosure generally relate to support structures for use in positioning solid phase microextraction sampling devices within openings of trees. In one example embodiment, a support structure generally includes a body configured to be received within an opening of a tree, a head coupled to the body, and a channel extending through the body and the head. The channel is configured to receive at least part of a solid phase microextraction sampling device therein.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a side elevation view of an example solid phase microextraction (SPME) assembly including one or more aspects of the present disclosure and operable to obtain a sample from a tree at a test site;

Figure 15:
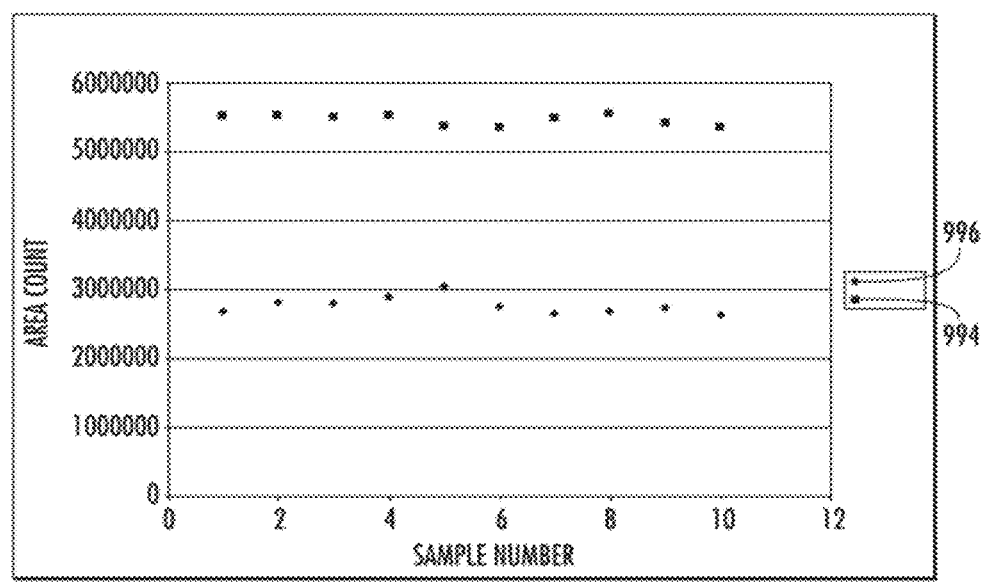
Figure 16:

FIG. 15 is a graph comparing detection values for TCE in samples prepared using tree cores and in samples prepared using tubing from an example sorption-based sampling assembly including one or more aspect of the present disclosure; and FIG. 16 is a plan view of example detection results of PCE using example sorption-based sampling assemblies including one or more aspects of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments of the present disclosure generally relate to determining the presence of compounds and/or the concentration of compounds in various structures located at a test site. Structures may include plants, buildings, or other environmental media located at a test site. Plants may include, for example, trees, deep-rooted grasses, deep rooted agronomic crops, soybeans, maize, wheat, other vegetation, etc. Buildings may include any man-made structures. And, other environmental media may include any other environmental media located at a test site such as, for example, groundwater, air, soil, rocks, etc.

For example, analysis techniques and/or devices disclosed herein may be used to determine presence and/or concentration of contaminant compounds in trees located on a test site (e.g., on a test site to be evaluated for presence of contaminants, etc.). These results may then be used to determine presence and/or concentration of contaminant compounds in the subsurface below the test site (e.g., in the groundwater below the trees at the test site, etc.). And, this information may then be used, for example, to delineate plumes of contaminants in the subsurface (including indications of the concentrations of such contaminants); to monitor and/or track the contaminants in the subsurface; to assess vapor intrusion potential of the contaminants into buildings; to project contaminant exposure history for volatile and/or semi-volatile organic compounds; to determine historical concentration gradients within the trees on the test site; to provide evidence of natural attenuation of contaminants by detecting degradation products; etc. Contaminants may include, but are not limited to, chlorinated-ethenes, -ethanes, and -methanes; chloroform; carbon tetrachloride; benzene; toluene; ethylbenzene; m-xylene; naphthalene; phenanthrene; fluoranthrene; cyclotrimethylenetrinitramine (RDX); trinitrotoluene (TNT); herbicides; pesticides; etc.

Analysis of a test site, using the techniques and/or devices disclosed herein, may include one or more of initial site analysis, initial discovery of subsurface contamination, spatial location of the subsurface contamination, concentration determination of the subsurface contamination, delineation of a contamination plume, etc. Analysis may include other operations within the scope of the present disclosure.

In one example embodiment of the present disclosure, analysis of a test site involves in-planta analysis of the test site to determine the presence and concentration of contaminant compounds in plants (particularly in trees) located on the test site. This information can be used to determine presence and concentration of the contaminant compounds in the subsurface below the test site.

For example, concentrations of contaminant compounds in the transpiration streams of plants are typically related to concentrations of the contaminant compounds in the subsurface below the plants. The concentrations of contaminant compounds in the transpiration streams of plants may follow a generally linear relationship with their concentrations in the subsurface below the plants, or they may follow any other suitable quantitative relationship within the scope of the present disclosure. As such, contaminant uptake in the plants at the test site may be determined and correlated (e.g., quantitatively correlated, spatially correlated, etc.) to contamination in the underlying subsurface (e.g., in the underlying groundwater, in the underlying soil, etc.).

In turn, the subsurface contaminants (e.g., located within a plume under the test site, etc.) may be mapped over a geographic area of the test site and/or monitored to determine extent, movement, etc. of the contaminants across the test site. Thus, such in-planta analysis can allow for rapid in-field investigations of the test site. And, using samples from the plants at the test site for determining presence and concentration of contaminant compounds at the test site may allow for testing in areas of the test site typically inaccessible to traditional sampling methods (e.g., sampling via drilled wells, etc.).

Figure 1:
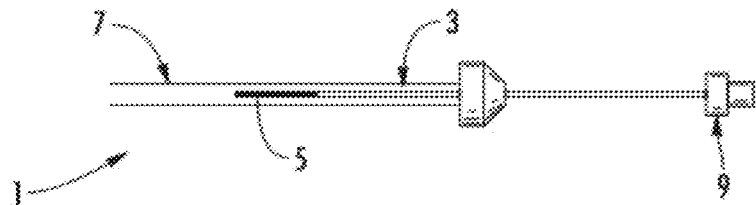
FIG. 1 is a side elevation view of a solid phase microextraction (SPME) assembly.
Figure 2:
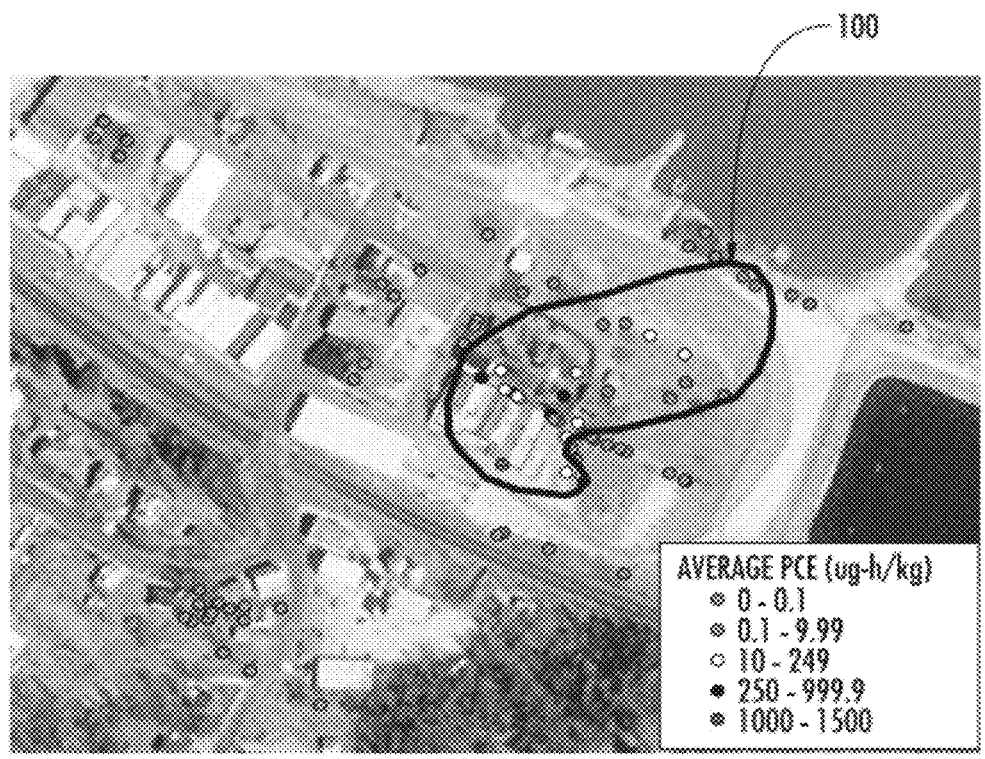
FIG. 2 is a plan view of an example delineation of a perchloroethylene (PCE) plume, with PCE concentration indicated in microgram-hours per kilogram (µg-h/kg)

FIG. 2 illustrates results of the application of an example in-planta analysis performed at a test site contaminated with perchloroethylene (PCE). Here, example analysis techniques and devices as disclosed herein were used to determine presence and concentration of PCE in plants located on the test site (with PCE concentration indicated in microgram-hours per kilogram (µg-h/kg)). These results were then used to determine presence and concentration of PCE in the groundwater under the test site (as generally known). And, this information in turn was then used to delineate a plume 100 of PCE in the groundwater. It should be appreciated that previous research has established a link of PCE in groundwater to PCE in overlying plant tissues (see, e.g., Struckhoff, G., J. G. Burken, and J. G. Schumacher (2005): "Phytoremediation of Vadose Zone VOCs," *Environmental Science and Technology*, 39(6) 1563-1568 (which is incorporated herein by reference); Ma, X. and J. G. Burken (2002): "VOCs Fate and Partitioning in Vegetation: Use of Tree Cores in Groundwater Analysis," *Environmental Science and Technology*, 36 (21) 4663-4668 (which is incorporated herein by reference); etc.).

Figure 3:
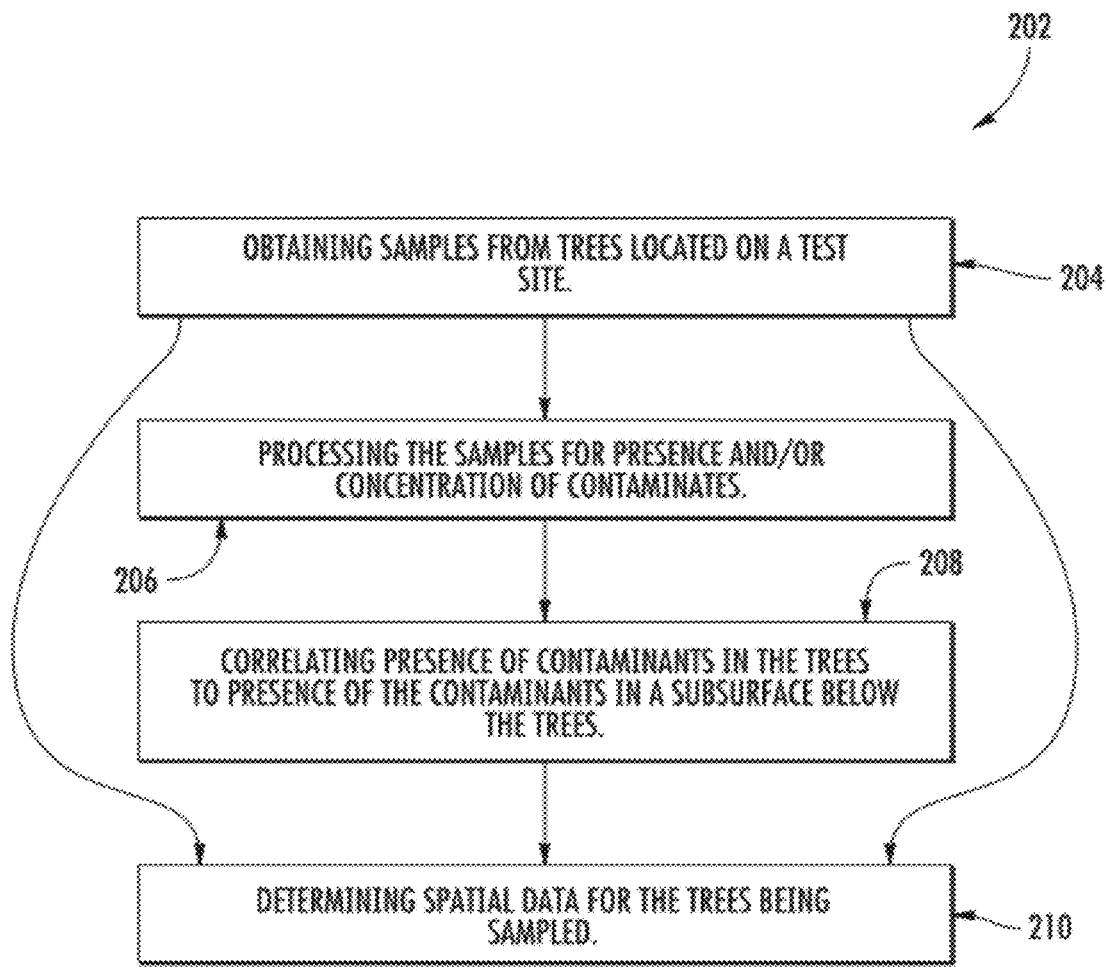
FIG. 3 is a flow diagram of an example method for use in determining the presence of at least one environmental contaminant in a tree located at a test site and then using that information to determine presence of the environmental contaminant in a subsurface under the tree.

With reference now to FIG. 3, an example method for determining the presence of an environmental contaminant in at least one tree located at a test site, and then using that information to determine the presence of the contaminant in a subsurface under the tree is indicated generally at reference number 202. The example method 202 generally includes obtaining samples from trees located on the test site (as indicated generally at reference number 204 in FIG. 3), and processing the samples for presence and/or concentration of contaminants (as indicated generally at reference number 206 in FIG. 3). To improve accuracy of the analysis and provide a satisfactory representation of any subsurface contaminants (e.g., location, concentration, etc.), more than one sample may be obtained from each tree and multiple samples may be obtained from a sufficient number of trees across the test site. Selection of trees to be sampled may depend on, among other things, geography, vegetation, development (e.g., rural development, residential development, commercial development, etc.), contamination, etc. of the test site. For example, similar species of trees may be sampled, similar sizes of trees may be sampled, etc.

In the example method 202, obtaining samples from the trees (as indicated generally at reference number 204 in FIG. 3) may generally include positioning (e.g., inserting, etc.) a sampling assembly (e.g., a solid phase microextraction (SPME) assembly, other sorption-based sampling assembly, etc.) into an opening of each of the trees, and leaving the sampling assembly within the respective opening for a sufficient time to allow any contaminant in the tree to sorb to the sampling assembly (e.g., to a SPME fiber, to other sorption-based materials, etc.). The sampling assemblies may be positioned within any suitable openings in the trees within the scope of the present disclosure (e.g., within a man-made opening, within a naturally-occurring opening, etc.). And, each sampling assembly may be located within an opening of the respective tree so as to avoid cross-contamination with air outside the tree (e.g., the sampling assembly may be substantially sealed within the opening of the tree, etc.). Further, the sampling assembly may be left within the respective opening for any desired and/or suitable amount of time, as will be described in more detail hereinafter.

Processing the samples (as indicated generally at reference number 206 in FIG. 3) generally includes removing the sampling assemblies from their respective openings in the trees at the test site, after being left within the opening for a desired and/or suitable amount of time, and placing the sampling assemblies in containers (e.g., sealed containers, etc.) for storage and/or transport. Subsequent testing of the sampling assemblies may then ensue using, for example, chemical analysis and/or physical analysis. Chemical analysis, for example, may include using one or more of (or combinations of) gas chromatography (GC), liquid chromatography (LC), mass spectrometry (MS), GC with detection and quantification via MS, LC with detection and quantification via MS, flame ionization detection (FID), electron capture detection (ECD), etc. Physical analysis may include, for example, visual inspection, weight recordation, etc. This testing may be done off-site in a laboratory or on-site as desired and within the scope of the present disclosure.

The results from processing the sampling assemblies (i.e., from the samples obtained using the sampling assemblies) may include identification of contaminants present in the sampling assemblies as well as determination of the concentrations of the contaminants. The identification and/or concentration information of the contaminants present in the sampling assemblies is typically directly indicative of the identification and/or concentration information of contaminants present in the trees being sampled.

The identification and/or concentration information of the contaminants present in the trees being sampled may next be correlated to the subsurface of the site (as indicated generally at reference number 208 in FIG. 3). For example, quantitative correlations may be established by obtaining one or more subsurface samples (e.g., groundwater samples, etc.) from one or more locations on the test site and comparing them to the processing results from the sampling assemblies. The subsurface samples may be obtained using traditional sampling methods (e.g., from sampling wells, etc.) at locations closely adjacent to at least one of the trees being sampled using the sampling assemblies. In this manner, presence and/or concentration of a contaminant in the tested tree (based on the test results of the sample taken from the tree using the sampling assembly) may be correlated to presence and/or concentration of the contaminant in the subsurface below the tree (based on the test results of the sample taken from the subsurface closely adjacent the tree using the traditional sampling methods).

The example method 202 may also include, before and/or after obtaining the samples (and/or after processing the samples), determining (e.g., recording, etc.) spatial data (e.g., coordinates, etc.) of the tree being sampled using, for example, global positioning system (GPS) equipment (as indicated generally at reference number 210 in FIG. 3). The contaminant information from the tree sample (e.g., type of contaminant, concentration of contaminant, etc.) can then be spatially correlated to the position, location, etc. of the tree from which the sample is obtained. This spatial correlation can be done independent of the quantitative correlation previously described, or in addition to the quantitative correlation. The results of the spatial correlation can then be plotted (e.g., using geographic information system software, etc.) to help graphically delineate a plume of the contaminant(s) under the test site (e.g., graphically delineate boundaries of a plume of the contaminant(s) under the test site, etc.). Further analysis of the graphical delineation may then take place, including, for example, comparing the plotted plume data to existing groundwater data to establish qualitative relationships; comparing the plotted plume data to historic subsurface contamination data to establish remediation patterns, transport patterns, etc.

It should be appreciated that various different sampling assemblies may be used to obtain samples from trees in accordance with the example method 202 previously described and illustrated in FIG. 3. While various example sampling assemblies are disclosed herein, it should be appreciated that other sampling assemblies may be used in accord with the example operations disclosed, for example, for use in evaluating contaminant presence and/or concentration in subsurface environments. For example, as previously stated a solid phase microextraction (SPME) assembly may be used, other suitable sorption-based sampling devices may be used, etc. within the scope of the present disclosure.

FIGS. 4-8 illustrate an example SPME assembly 320 operable to obtain samples from trees at a test site (e.g., in accordance with the example method 202 previously described and illustrated in FIG. 3, etc.). As shown in FIG. 4, the example SPME assembly 320 generally includes a support 322 and a SPME sampling device 324. The support 322 is operable for positioning the SPME sampling device 324 within an opening of a tree (e.g., bore opening 349 of tree 347 in FIGS. 6-8, etc.) at the test site. The support 322 includes a generally hexagonal outward head 326 and a generally cylindrical inward shaft 328 extending away from the head 326 (and coupled to the head 326). The configuration (e.g., size, shape, construction, etc.) of the head 326 may allow the head 326 to generally abut against an outer portion of a tree when the shaft 328 is positioned within an opening of the tree. This may help seal the support 322 against the tree and help inhibit mass transfer of compounds between the tree and external surroundings through the opening. The support 322 may be constructed of an inert material (e.g., aluminum, silicon, etc.) within the scope of the present disclosure.

The shaft 328 of illustrated SPME assembly support 322 includes exterior threads 330 extending around the shaft 328. The threads 330 are configured (e.g., sized, shaped, constructed, etc.) to promote inserting the support 322 into an opening of a tree (e.g., bore opening 349 of tree 347 in FIGS. 6-8, etc.). For example, the threads 330 may be configured (e.g., sized, shaped, constructed, etc.) to engage an inner portion of the tree at the opening in the tree to facilitate rotating, threading, screwing, etc. the support 322 into the tree. In addition, the hexagonal shape of the head 326 may allow for grasping the head 326 with a tool (e.g., a wrench, etc.) to further help insert (e.g., rotate, thread, screw, etc.) the support 322 into the tree opening.

It should be appreciated that the shaft 328 of the SMPE assembly support 322 may include an outer diameter sized to fit within an opening of a desired tree (e.g., bore opening 349 of tree 347 in FIGS. 6-8, etc.), and a length sized to extend a distance into the tree through the bore opening. In the illustrated embodiment, for example, the shaft 328 includes an outer diameter dimension of about 8 millimeters and a length dimension of about 21 millimeters. However, in other example embodiments, supports may include other dimensions as desired and as required by trees from which samples are to be obtained.

With continued reference to FIG. 4, the SPME sampling device 324 of the illustrated SPME assembly 320 generally includes a housing 332 extending away from a neck 334, and a fiber 336 having a polymer coating 338 enclosed within the housing 332. A plunger 340 is operably coupled to the fiber 336 through the neck 334 for selectively moving the fiber 336 relative to the housing 332. For example, the plunger 340 may be moved in a direction generally toward the neck 334 to move the fiber 336 generally outwardly of the housing 332, and the plunger 340 may be moved generally away from the neck 334 to move the fiber 336 generally inwardly of the housing 332.

The fiber coating 336 of the SPME sampling device 324 may include any suitable polymer having, for example, relatively high sorption capacities that, when exposed to compounds of specific chemical natures, allow the compounds to sorb to the polymers proportionately to the concentration of the compounds in a surrounding environment (e.g., within a tree being sampled, etc.). It should be understood that different fibers (e.g., fibers having different polymers, etc.) may be used with the SPME sampling device 324 for sampling operation within the scope of the present disclosure. And, the specific type of fiber used may depend on the suspected contaminants present at a test site. For example, polydimethylsiloxane (PDMS) fibers may be used for sampling polycyclic aromatic hydrocarbons (PAHs) such as napthalene or compounds of similar properties; carboxene (CAR) fibers may be used for sampling highly volatile compounds such as chlorinated ethenes or ethanes; composite CAR/PDMS fibers may be used for sampling the same compounds or mixtures thereof; etc.

Figure 5:
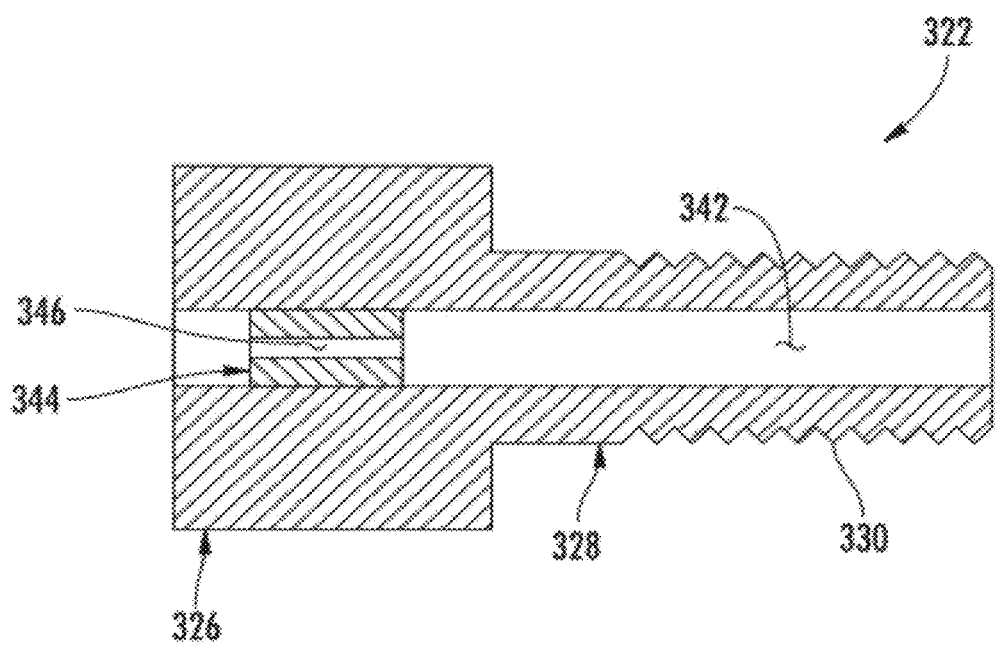
FIG. 5 is a longitudinal section view of a support of the SPME assembly of FIG. 4.

With additional reference now to FIG. 5, the support 322 of the illustrated SPME assembly 320 includes a central channel 342 extending through the support 322 (e.g., through the head 326 of the support 322 and through the shaft 328 of the support 322, etc.) for receiving the SPME sampling device 324 into the support 322 during sampling operation. For example, the central channel 342 is sized to receive at least part of the housing 332, the neck 334, and the plunger 340 of the support 322 into the central channel 342 as desired. The housing 332 may extend at least partially into the central channel 342, or the housing 332 may extend completely through the central channel 342 within the scope of the present disclosure.

A sleeve 344 (e.g., a ferrule, etc.) is positioned generally within the central channel 342 of the support 322 for use in holding the SPME sampling device 324 within the support 322 (as the central channel 342 of the illustrated support 322 is generally larger than the housing 332 of the SPME sampling device 324). The sleeve 344 includes a central opening 346 through which at least part of the housing 332 of the SPME sampling device 324 may be positioned during sampling operation. The sleeve 344 is located within the central channel 342 a distance into the central channel 342. This allows the neck 334 of the SPME sampling device 324 to be positioned within the central channel 342, adjacent the sleeve 344, when the housing 332 (and the fiber 336) of the SPME sampling device 324 are received into the central channel 342 (and through the central opening 346 of the sleeve 344). The sleeve 344 is configured to help centrally position the SPME sampling device 324 within the support 322, and may help stabilize the SPME sampling device 324 so that the fiber 336 thereof does not touch the support 322 or an inner portion of a tree during sampling operation.

In the illustrated embodiment, the sleeve 344 includes an outer diameter dimension of about 3.6 millimeters (generally corresponding to an inner diameter of the central channel 342 of the support 322), and a length dimension of about 4.4 millimeters. And, the sleeve 344 is positioned within the central channel 342 of the support 322 about 4.4 millimeters from an outer end portion of the head 326 of the support 322. In addition, the sleeve 344 may be formed at least partly from a silicon material, an aluminum material, combinations thereof, etc. to help seal and support the SPME sampling device 324 within the support 322 and/or to help seal the fiber 336 of the SPME sampling device 324 within sleeve 344.

Figure 6:
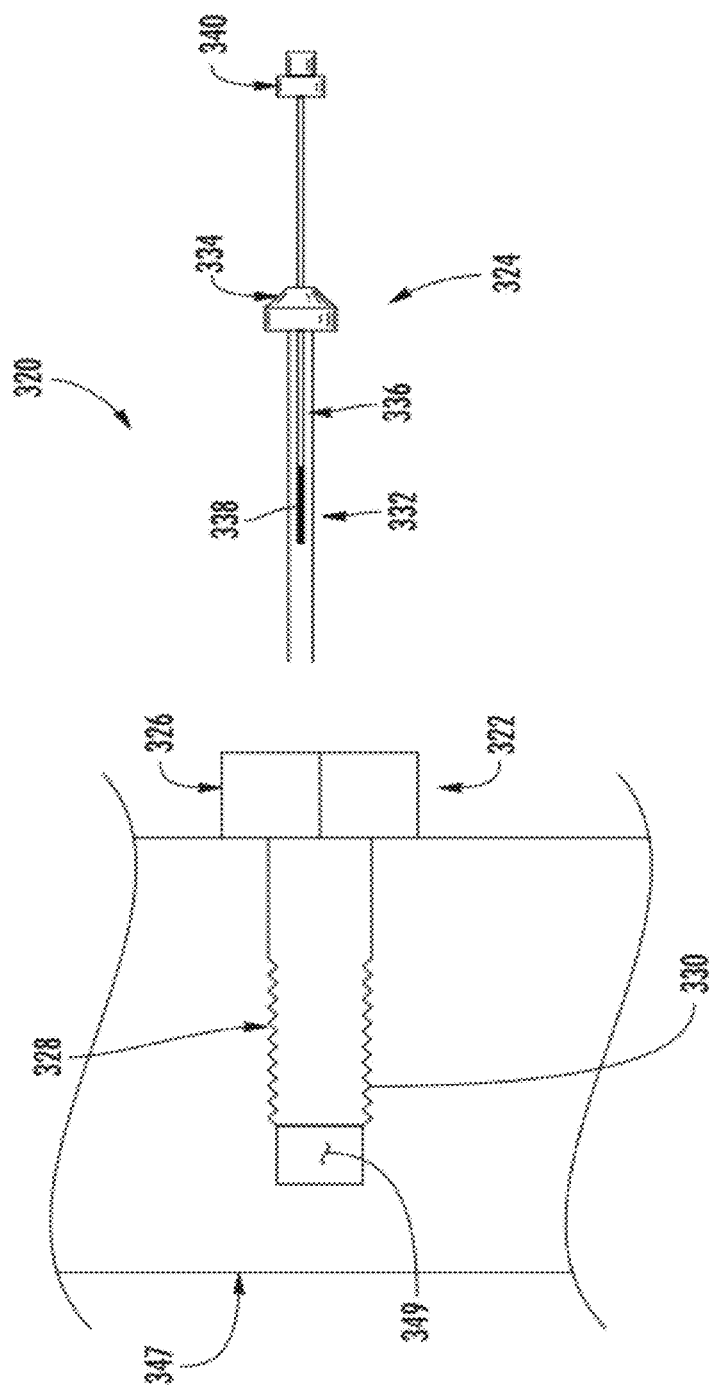
FIG. 6 is a fragmentary side elevation view of a tree with the support of the SPME assembly of FIG. 4 shown inserted into a bore opening of the tree and with a SPME sampling device of the SPME assembly shown in a position adjacent the support.
Figure 7:
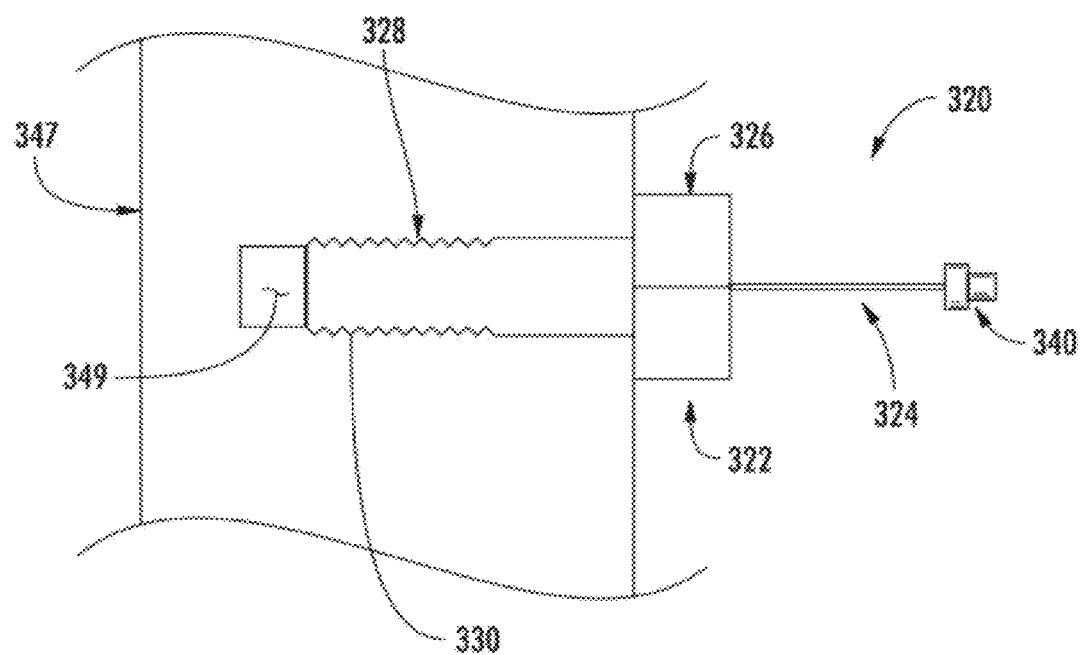
FIG. 7 is a fragmentary side elevation view similar to FIG. 6 with the SPME sampling device shown positioned generally within the support.
Figure 8:
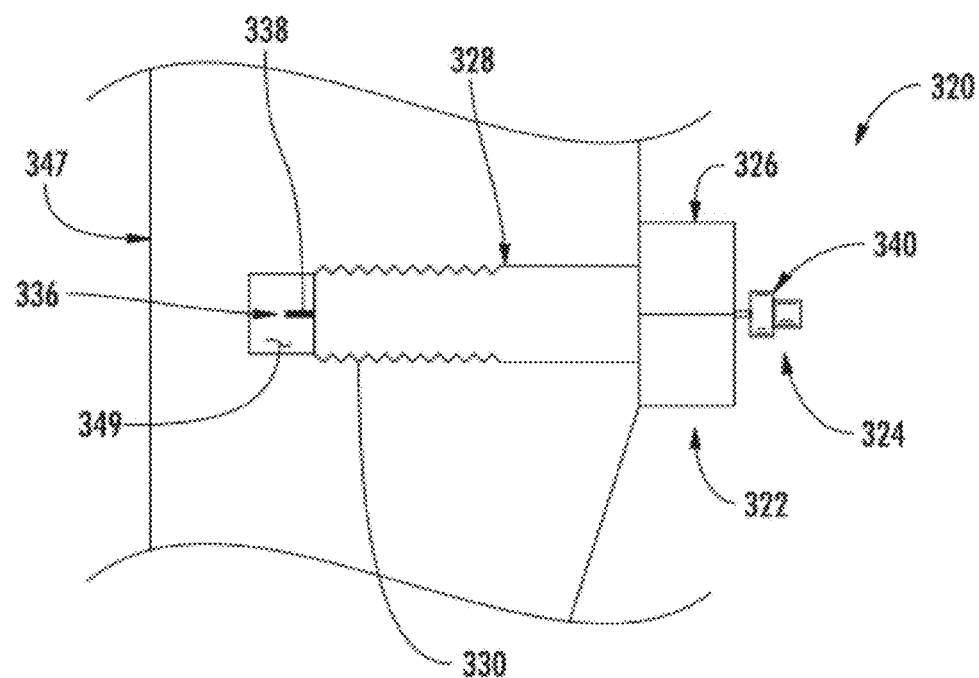
FIG. 8 is a fragmentary side elevation view similar to FIG. 7 with a plunger of the SPME sampling device shown depressed to expose a fiber of the SPME sampling device into the bore opening of the tree.

With reference now to FIGS. 6-8, an example operation for using the SPME assembly 320 to obtain a sample from a tree 347 at a test site will be described. A core (not shown) is initially removed from the tree 347 to create a bore 349 (broadly, an opening) configured to receive the SPME assembly 320 into the tree 347 (via the bore 349). The removed core may be generally uniform in shape and may have, for example, a diameter of about 5 millimeters and a length of about 40 millimeters thus leaving an appropriate size bore 349 for the SPME assembly 320. However, a differently sized core and/or a non-uniform core may be taken from the tree 347 within the scope of the present disclosure. The core may be removed using a suitable coring device, drill, etc. In addition, the bore 349 may be sized to receive more than one SPME assembly 320 within the bore 349 within the scope of the present disclosure. The core may also be analyzed as desired for contaminant presence and/or concentration within the scope of the present disclosure.

After creating the bore 349 in the tree 347, the support 322 of the SPME assembly 320 is positioned in the bore 349 (FIG. 6), and the SPME sampling device 324 is then positioned within the support 322 (e.g., within the central channel 342 extending generally through the support 322, etc.) (FIGS. 7 and 8). Positioning the support 322 within the bore 349 may include threading, screwing, etc. the support 322 into the tree 347 (through the bore 349) so that the shaft 328 is located within the bore 349 and the head 326 generally abuts an outer surface of the tree 347. The SPME sampling device 324 can then be positioned within the support 322 (which is positioned within the tree bore 349) by moving the housing 332 through the central channel 342 of the support 322 (and through the central opening 346 of the sleeve 344) until the neck 334 of the SPME sampling device 324 is adjacent the sleeve 344 of the support 322. During this operation, the plunger 340 is positioned in a generally extended position relative to the neck 334 so that the fiber 336 is maintained generally within the housing 332 (e.g., to protect the fiber 336 from damage, etc.).

The support 322 operates to help properly position the SPME sampling device 324 within the tree bore 349. In addition, the support 322 may help stabilize the SPME sampling device 324 within the tree bore 349 so that it does not touch the tree mass within the bore 349 and/or does not break (or become damaged) if bumped from outside the tree 347. Moreover, the support 322 may be configured (e.g., sized, shaped, constructed, etc.) to substantially seal the tree bore 349 to prevent mass transport of any contaminants from within the tree 347, through the bore 349, and out of the tree 347 to external surroundings (and vice versa).

As shown in FIGS. 7 and 8, after the SPME sampling device 324 is positioned within the support 322 (and within the tree 347), the plunger 340 of the SPME sampling device 324 can be operated (e.g., depressed, moved generally toward the neck 334, etc.) to move the fiber 336 through the housing 332 and into (and generally through) the central opening 346 of the sleeve 344 to expose the fiber 336 for sampling operation. It should be appreciated that the fiber 336 may be extended out of the housing 332 and into the central channel 342 of the support 322 (and possibly through the central channel 342 and into the tree bore 349) any desired length for sampling operation. For example, the fiber 336 may be extended out of the housing 332 a full length of about 10 millimeters as generally shown in FIG. 8 (e.g., for equilibrium analysis, etc.). Or alternatively, the fiber 336 may be only partially exposed from the housing 332 or left retracted in the housing 332 to perform, for example, time weighted average (TWA) analyses. This may slow sorption of compounds to the fiber 336 such that analysis may be performed over longer periods of time. Thus, the amount of extension (if any) of the fiber 336 out of the housing 332 may depend on the type of analysis being performed (e.g., equilibrium analysis, TWA analysis, etc.). And, the type of analysis being performed may depend on the particular component(s) present in the tree 347 (or other tree) to be sampled, on the desired accuracy, etc.

Once sampling operation begins, the SPME assembly 320 is left in the tree bore 349 for a desired sampling duration. The SPME assembly 320 can be left in the tree bore 349 for a variety of time periods based upon, for example, the contaminants targeted, the accuracy required, the sampling approach desired (equilibrium analysis, TWA analysis, etc.), the type of fiber being used with the SPME sampling device 324, etc. In addition, the type of analysis being performed may depend on the component(s) targeted, on the desired accuracy, on the type of fiber being used with the SPME sampling device 324, etc. For example, for equilibrium sampling with a polydimethylsiloxane (PDMS) fiber, three to ten minutes are expected to be adequate. In TWA analysis for low concentrations, about seventy-five minutes is adequate to allow sufficient sorption of low concentration contaminants (e.g., contaminants diffusing from within the tree 347 through the bore 349 opening during sampling, etc.) to the fiber 336. In other example embodiments, fibers may be left in trees for days or even weeks.

When sampling is complete, the SPME sampling device 324 is removed from the tree bore 349 and placed in a substantially sealed container (e.g., in packaging provided by the manufacturer of the SPME sampling device 324, and further covered with a silicon cap, etc.) (not shown) to help inhibit mass transport of the sorbed contaminants between the fiber 336 and the external surroundings. The container and SPME sampling device 324 are then stored for subsequent processing as described next. The contaminants remain incorporated with the fiber 336 until desorption and analysis is desired.

As previously stated, processing the SPME sampling device 324 generally includes performing chemical analysis on the fiber 336 of the SPME sampling device 324. As an example, this processing may be done on-site using a portable GC. Here, the SPME sampling device 324 (and sample included thereon) is removed from storage, and the housing 332 is positioned within an injection port of the GC. The plunger 340 is then depressed to move the fiber 336 out of the housing 332 and into a heated column of the GC. The heat desorbs any contaminants incorporated into the fiber 336 so that subsequent gas chromatography analysis can take place. The subsequent GC analysis may include identification of contaminants present in the sample as well as determination of the concentration of contaminants present in the sample. The identification and/or concentration information of the contaminants present in the sample from the SPME sampling device 324 can then be correlated to the subsurface of the test site. For example, quantitative correlation may be established by obtaining one or more groundwater samples from one or more locations on a site and comparing them (e.g., compound concentrations in the samples, etc.) to the processing results.

In other example operations, supports and SPME sampling devices of SPME assemblies may be positioned in openings of trees as single units. For example, a SPME sampling device may initially be positioned within a support of a SPME assembly, and then the joined SPME sampling device and support can together be positioned (e.g., screwed, etc.) within an opening of a tree (e.g., within a bore of a tree, etc.).

Figure 9:
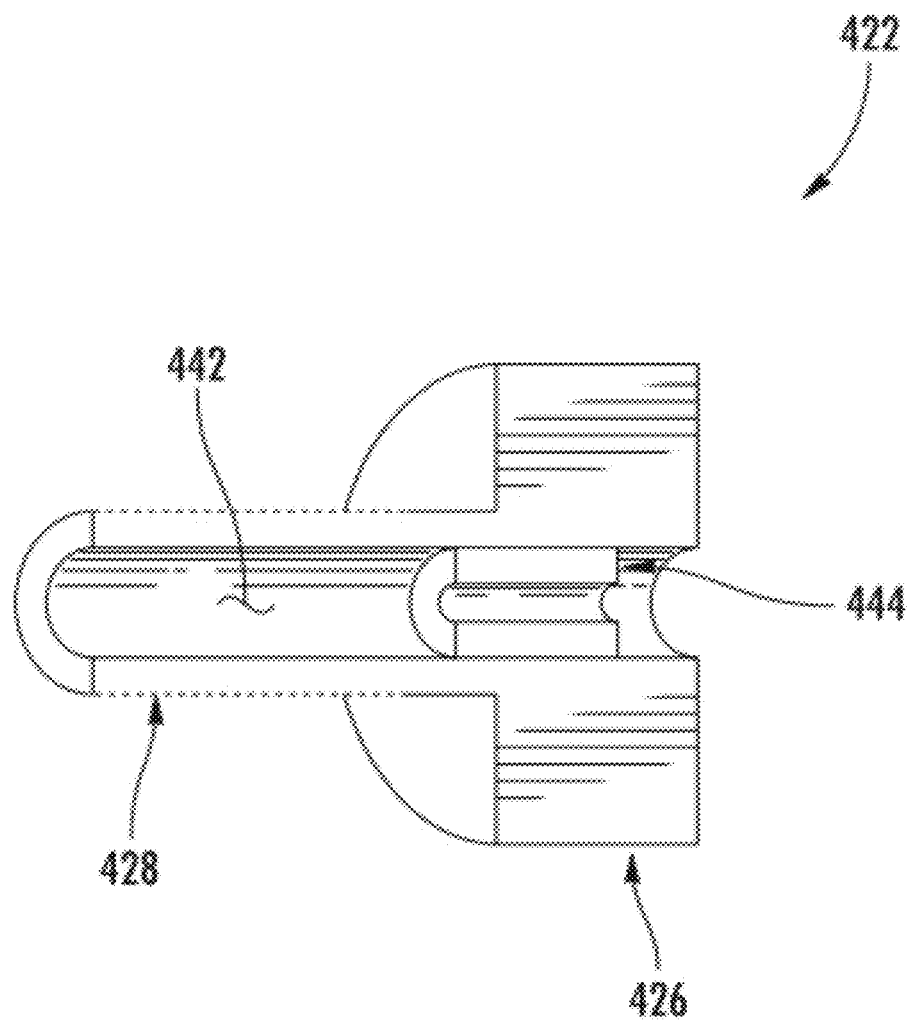
FIG. 9 is a perspective longitudinal section view of an example support suitable for use in positioning a SPME sampling device in an opening of a tree.

FIG. 9 illustrates another example embodiment of a support 422 suitable for use in positioning a SPME sampling device (not shown) in an opening of a tree (e.g., within a bore formed in a tree, etc.) for sampling. The support 422 is similar to the SPME sampling device support 322 previously described and illustrated in FIGS. 4-8. In this embodiment, the support 422 includes a generally cylindrical head 426 and a generally cylindrical inward shaft 428 extending away from the head 426. A central channel 442 extends generally through the head 426 and the shaft 428 of the support 422, and a sleeve 444 (e.g., a ferrule, etc.) is positioned within the central channel 442 for use in supporting a SPME sampling device within the support 422, for example, for sampling operation.

Figure 10:
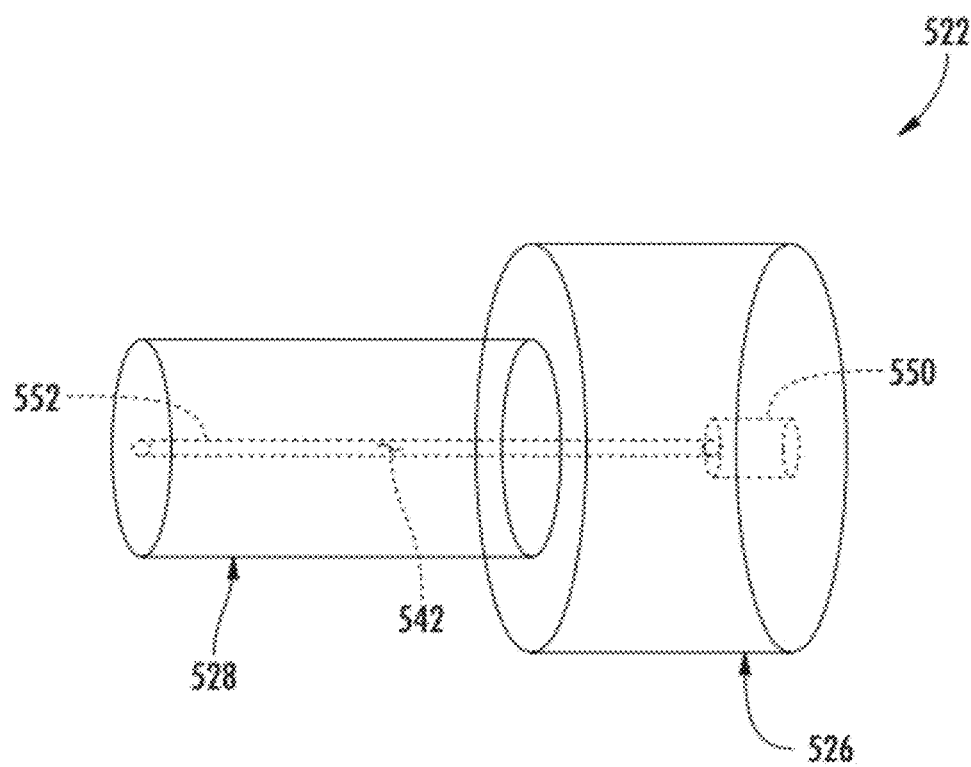
FIG. 10 is a perspective view of another example support suitable for use in positioning a SPME sampling device in an opening of a tree, with a central channel of the support configured for receiving at least part of the SPME sampling device therein shown in broken lines.

FIG. 10 illustrates still another example embodiment of a support 522 suitable for use in positioning a SPME sampling device (not shown) in an opening of a tree (e.g., within a bore formed in a tree, etc.) for sampling. The support 522 is generally similar to the SPME sampling device support 322 previously described and illustrated in FIGS. 4-8. The illustrated support 522 includes a generally cylindrical head 526 and a generally cylindrical inward shaft 528 extending away from the head 526. A central channel 542 extends generally through the head 526 and the shaft 528 for receiving a SPME sampling device into the support 522 (e.g., for receiving a housing of the SPME sampling device into the support 522).

In this embodiment, the central channel 542 includes an enlarged outer section 550 located generally within the head 526 of the support 522, and a narrowed inner section 552 located generally within the shaft 528. When a SPME sampling device is positioned within the support 522 of this embodiment, at least part of a neck of the SPME sampling device may be received within the enlarged outer section 550 of the central channel 542 when a housing the SPME sampling device is positioned within the narrowed inner section 552 of the central channel 542. This may provide additional support for the SPME sampling device during sampling operation.

Figure 11:
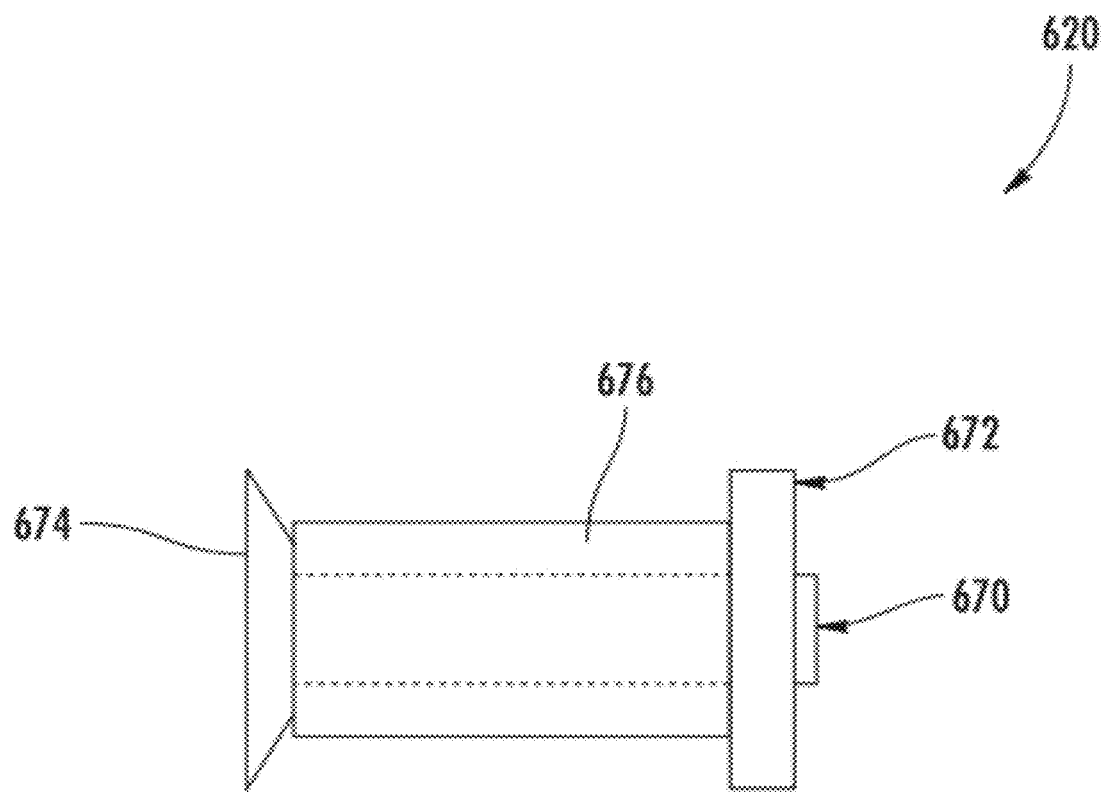
FIG. 11 is a side elevation view of an example sorption-based sampling assembly operable to obtain a sample from a tree at a test site.

FIG. 11 illustrates an example embodiment of another sorption-based sampling assembly 620 operable to obtain samples from trees (e.g., trees, etc.) at a test site (e.g., in accordance with the example method 202 previously described and illustrated in FIG. 3, etc.). For example, the illustrated sampling assembly 620 may be positioned within an opening of a tree (e.g., within a bore formed in a tree, etc.) for sampling operation, wherein the results may then be used to help determine subsurface contamination at the test site.

The illustrated sampling assembly 620 of this embodiment generally includes a body 670 having a forward flange 672 and a rearward flange 674, and a tubing 676 disposed over the body 670 between the two flanges 672 and 674. The body 670 may include any suitable material such as, for example, a #4 screw having a head (broadly a flange 674) at one end and a #4 nut (broadly a flange 672) fastened to the screw at a generally opposite end. In addition, any suitable tubing material may be used such as, for example, silicon tubing (e.g., Tygon®, etc.), etc. Silicon tubing has a generally high sorption capacity that, when exposed, for example, to contaminants within a tree (e.g., contaminants diffusing from within a tree through a bore opening of the tree, etc.) allow the contaminants to sorb thereto proportionately to the concentration of the contaminants in the tree (and thus proportionately to the contaminants in the subsurface below the tree). In other example embodiments, tubing may include a hydrophobic polymer, other suitable materials, etc.

An example operation for using the illustrated sampling assembly 620 to obtain a sample from a tree at a test site will now be described. A generally uniform core is initially removed from a selected tree to create a bore (broadly, an opening) in the tree, and the sampling assembly 620 is then positioned within the bore (e.g., substantially within the tree bore, etc.). A seal (e.g., a silicon body, a foil body, etc.) may then be positioned over the bore and/or within the bore over the sampling assembly 620 to substantially seal the sampling assembly 620 within the bore and to prevent mass transport of any contaminants between the tree bore and the external surroundings.

Once sampling operation begins, the sampling assembly 620 is left in the tree bore for a desired sampling duration. The sampling assembly 620 may be left in the tree bore for a variety of time periods depending upon, for example, the contaminants targeted, the accuracy required, the sampling approach desired (equilibrium analysis, TWA analysis, etc.), the type of tubing being used with the sampling assembly 620, etc. For example, the sampling assembly 620 may be left in the tree for several days to allow sufficient sorption of any contaminants to the tubing 676 (e.g., to establish an equilibrium concentration, etc.). However, the sampling assembly 620 may be left in the tree for a longer or shorter duration within the scope of the present disclosure (e.g., minutes, days, weeks, etc.).

When sampling is complete, the sampling assembly 620 is removed from the tree bore and the tubing 676 is removed and placed in a substantially sealed container (e.g., in a crimp-top vial, etc.) to help inhibit mass transport of the sorbed contaminants between the tubing 676 and the external surroundings. The container and tubing 676 are then stored for subsequent processing as described next. For example, the container and tubing 676 may be stored in a cooled environment to help inhibit early desorption. The contaminants remain incorporated with the tubing 676 until desorption and analysis is desired. In other example embodiments, entire sampling assemblies may be sealed in containers and stored for subsequent processing.

Processing the stored tubing 676 generally includes performing chemical analysis on the tubing 676. This may include using one or more of gas chromatography (GC), liquid chromatography (LC), mass spectrometry (MS), GC with detection and quantification via (MS), LC with detection and quantification via MS, flame ionization detection (FID), electron capture detection (ECD), combinations thereof, etc.

As an example, processing the stored tubing 676 may be done on-site using a portable GC. Here, headspace from the container holding the tubing 676 is sampled (e.g., using a syringe, etc.) and injected into the GC for GC analysis. The container (and tubing therein) may be heated prior to taking the headspace sample to help volatilize any contaminants incorporated with the tubing 676. The GC analysis may include identification of contaminants present in the sample as well as determination of the concentration of contaminants present in the sample from the tubing 676.

The identification and/or concentration information of the contaminants present in the sample from the tubing 676 can then be correlated to the subsurface of the site. For example, quantitative correlation may be established by obtaining one or more groundwater samples from one or more locations on a site and comparing them (e.g., compound concentrations in the samples, etc.) to the processing results.

As another example, processing the stored tubing 676 may be done in a laboratory environment using an auto-sampler in connection with a GC-MS. Here, the auto-sampler is used to sample headspace from the container holding the tubing 676 and inject the headspace sample into the GC-MS for GC-MS analysis. The container (and the tubing 676 therein) may be heated by the auto-sampler prior to taking the headspace sample to help volatilize any contaminants incorporated with the tubing 676. Again, the GC-MS analysis may include identification of contaminants present in the sample from the tubing 676 as well as determination of the concentration of contaminants present in the sample. The identification and/or concentration information of the contaminants present in the sample from the tubing 676 can then be correlated to the subsurface of the site.

Before and/or after sampling (and/or after processing the sample), spatial data of the tree selected for sampling can be recorded using global positioning system (GPS) equipment. The contaminant information from the tubing (e.g., type of contaminant, concentration of contaminant, etc.) can then be spatially correlated to the position of the tree on the test site. This spatial correlation data can then be plotted (e.g., using geographic information system software, etc.) to help graphically delineate subsurface contamination for the test site (e.g., graphically delineate boundaries of a plume of the contaminant(s) under the test site, etc.).

The sampling assembly 620 of this example embodiment is a substantially durable assembly that, for example, can be used by a person with little or no knowledge, experience, etc. with sampling operation to obtain a sample without substantive risk, concern, etc. of damage to the sampling assembly 620 or contamination of the sample. In addition, samples taken using the sampling assembly 620 of this embodiment may provide improved detection (see, e.g., Example 2 hereinafter). This can allow for transporting the sample from a site to, for example, a laboratory for subsequent testing without significant concern of sample dilution. Thus, the sampling assembly 620 may be used (e.g., mailed, etc.) at a contaminated site, for example, by an owner of the site, a worker at the site, etc. and then safely transported (e.g., mailed, etc.) to, for example, a laboratory for subsequent analysis without significant risk of sample loss and/or without the need for experienced technicians to travel to the site to obtain the sample. Moreover, multiple samples may be taken with the sampling assembly 620 in a short time frame (e.g., one-hundred eighty samples a day, etc.) such that large areas can be sampled relatively quickly, large numbers of samples can be processed for give test sites (e.g., to improve accuracy, etc.), etc.

Figure 12:
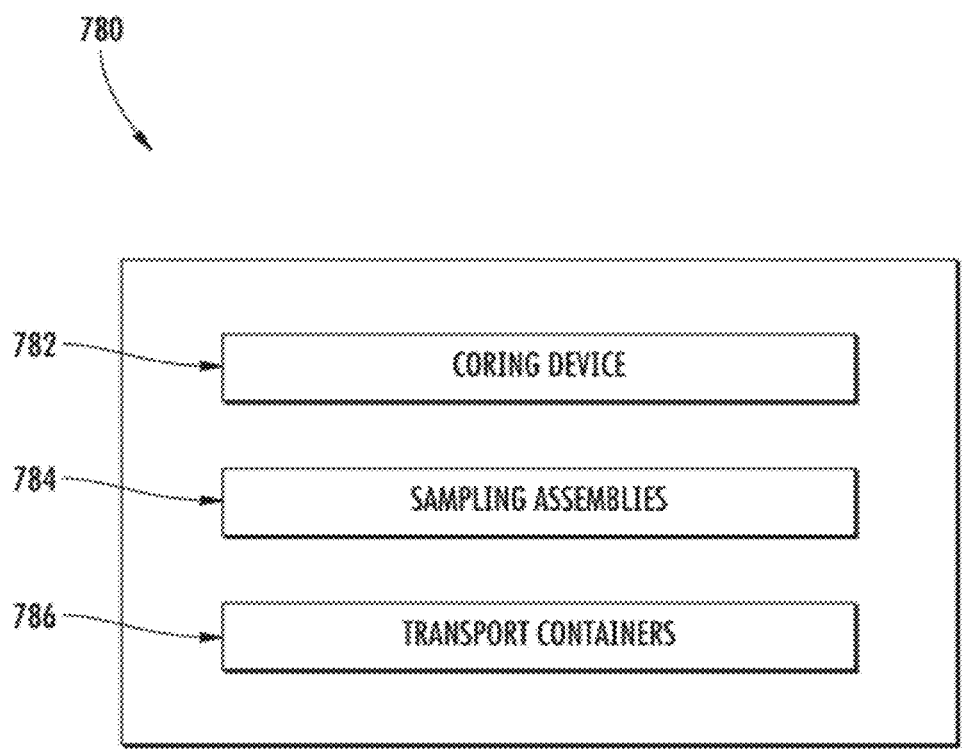
FIG. 12 is a schematic illustration of an example in-planta analysis kit suitable for use in obtaining samples from trees at a test site.

FIG. 12 illustrates an example embodiment of an in-planta analysis kit 780 for in obtaining samples from trees at a test site (e.g., in accordance with the example method 202 previously described and illustrated in FIG. 3, etc.). The kit 780 may be provided to the site (e.g., to the owner of the site, to workers at the site, etc.) for use in collecting samples as part of a contamination investigation on the site (e.g., without requiring other individuals to travel to the site to take the samples, etc.).

The illustrated kit 780 generally includes a coring device 782 for removing cores from trees on the site to be sampled such as trees, and one or more sampling assemblies 784 (e.g., one or more of sampling assembly 320, one or more of sampling assembly 620, etc.) for positioning within openings in the trees (e.g., within bores formed in trees using the coring device, etc.). The illustrated kit also includes one or more transport containers 786 (e.g., vials having sealing capabilities (e.g., screw-top vials, crimp top vials, etc.) for containing at least part of at least one of the sampling assemblies 784 exposed to compounds in the trees (e.g., contaminants, etc.)) for subsequently shipping the samples (e.g., to a laboratory, etc.) for testing.

The following examples are exemplary in nature. Variations of the following examples are possible without departing from the scope of the disclosure.

EXAMPLES

Example 1

Tree core and SPME sampling device samples (using CAR/PDMS fibers) were taken from five separate trees at a site in New Haven, Mo. The sampled trees included poplar trees and willow trees, and previous investigations indicated that at least PCE was present in the trees on this site.

SPME assembly supports and SPME sampling devices as disclosed herein were used in the analysis. The supports and SPME sampling devices were inserted into the trees in bore openings left by the removed cores. The sampling time began when the SPME sampling device was inserted into the support and lasted about 75 minutes. After sampling was complete, the SPME sampling devices were removed from the supports, capped with a Teflon® cap, and stored in storage boxes. The fibers of the SPME sampling devices were then stored at room temperature overnight before gas chromatography analysis.

Figure 13:
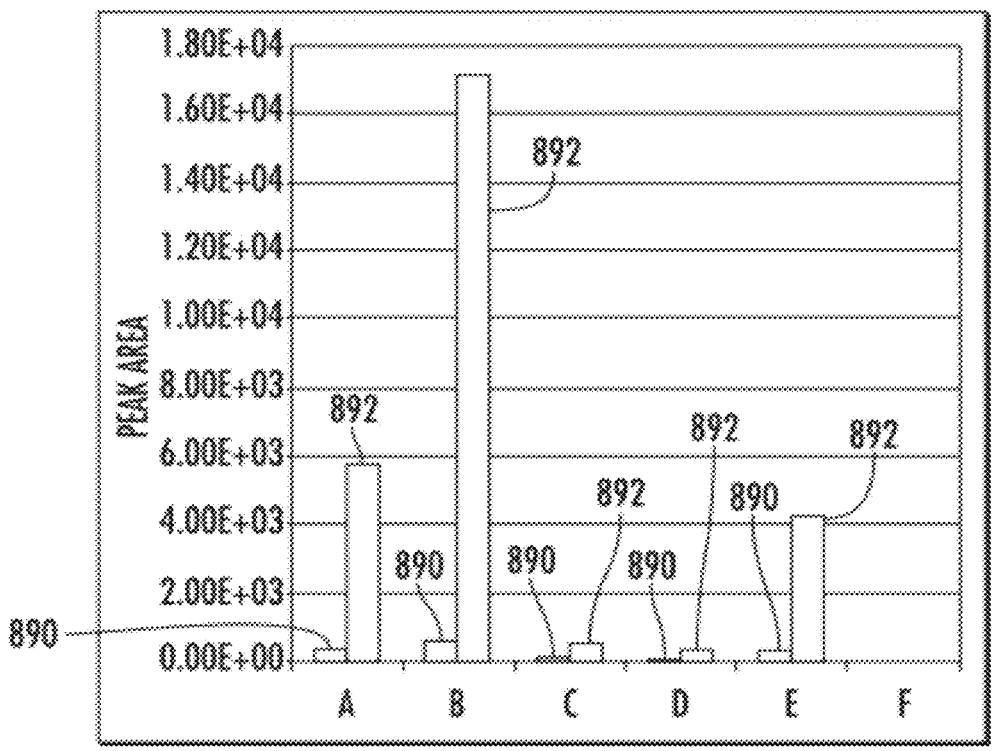
FIG. 13 is a graph comparing detection values for PCE in samples prepared using tree cores and in samples prepared using example SPME assemblies.
Figure 14:
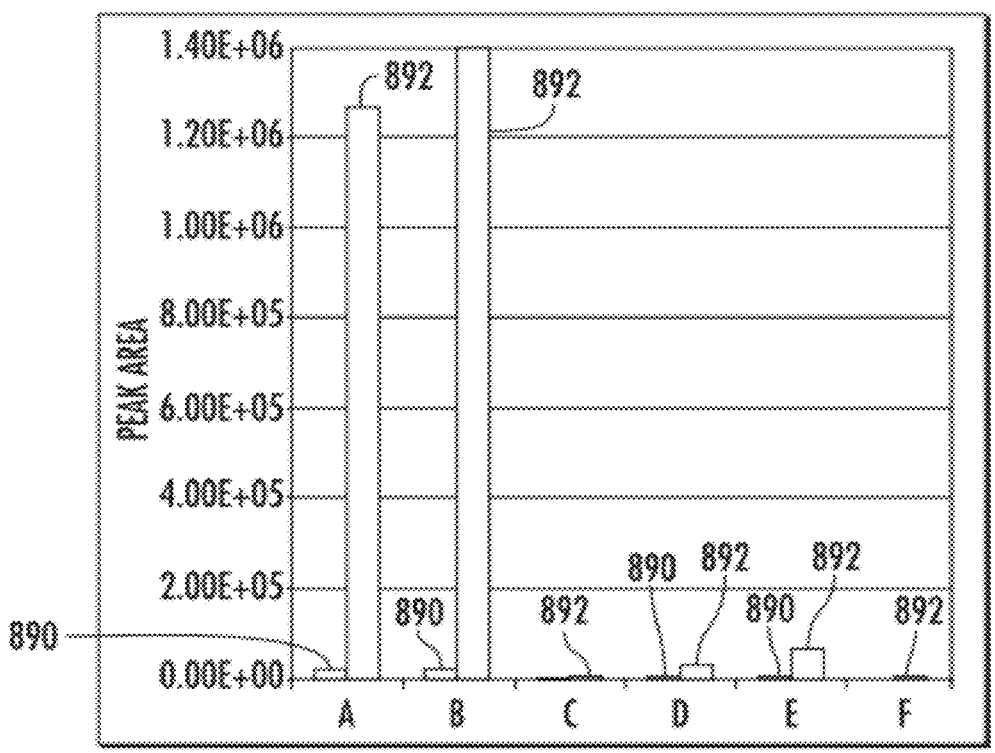
FIG. 14 is a graph comparing detection values for trichloroethylene (TCE) in samples prepared using tree cores and in samples prepared using example SPME assemblies.

The results of the analysis of the tree core samples (indicated at reference number 890) and the SPME sampling device samples (indicated at reference number 892) are comparatively shown in FIGS. 13 and 14. FIG. 13 illustrates results for PCE, and FIG. 14 illustrates results for TCE, which was also detected. The SPME sampling device samples showed substantially higher detection values than the core samples. For example, sampling with the SPME sampling devices resulted in detection values at least about six times higher for TCE and at least about five times higher for PCE. These results indicate a clear increase in sensitivity and abilities to detect contaminants at lower concentrations.

Example 2

Tests were conducted to compare detection values between a tree core sample and samples collected using a sampling assembly having silicon tubing (e.g., sampling assembly 620 such as that shown in FIG. 11, etc.). Ten samples were compared. Wood tissue samples were prepared using a 5 millimeter diameter dowel rod of poplar wood. The sampling assemblies were prepared using #4 screws having heads at one end and #4 nuts fastened to the screws at generally opposite ends, and Tygon® tubing positioned over the screws between the heads and the nuts.

The tree core samples and the sampling assemblies were both placed in a 100 milliliter beaker, divided by aluminum foil. The 100 milliliter beaker was then placed within a 300 milliliter beaker having PCE and TCE therein. A lid was then placed over the 300 milliliter beaker so that the tree core samples and the sampling assemblies were each exposed to the PCE and TCE in gas phase. The tree core samples and the sampling assemblies were each exposed for three weeks to allow them to reach equilibrium with the surrounding environment. After three weeks, the tree core samples and the silicon tubing samples (from the sampling assemblies) were removed, placed in separate vials, and capped. The samples were analyzed using a headspace auto-sampler and gas chromatography.

The results of the analysis for PCE are shown in FIG. 15 for this example. The silicon tubing samples (indicated at reference number 994) show a significantly higher analytic response than the tree core samples (indicated at reference number 996). Peak responses for the silicon tubing were at least twice as high as corresponding peak responses for the tree core samples.

Example 3

In this example, in-planta analysis was performed on a generally urban test site in Ontario, Canada using multiple ones of the sampling assembly 620 shown in FIG. 11. For example, each sampling assembly generally included a #4 screw having a head at one end and a #4 nut fastened to the screw at a generally opposite end, and Tygon® tubing positioned over the screw between the head and the nut. And, in preparation for sampling operation, the Tygon® tubing (e.g., having a mass of about 0.5 grams, etc.) was placed in a methanol bath for at least about twenty-four hours and then placed in a drying oven at about 100 degrees Celsius to remove any volatile organic compounds that could have been absorbed during preparation.

Tree cores were removed from trees across the test site, and sampling assemblies were placed in various ones of the bores left in the trees. The sampling assemblies were left in the tree bores for about fourteen to sixteen days, at which time they were collected from the tree bores, stored in sealed containers, and transported to a laboratory for testing. GC-MS analysis was used to determine presence and detection amounts (e.g., area count, etc.) of PCE at the test site. FIG. 16 illustrates the ultimate detection results for PCE at the test site (e.g., presence and area count, etc.) (ND indicates sample locations where PCE was not detectable). In particular, the results correlated well to the boundaries of the PCE plume as determined using traditional sampling operations (e.g., sampling wells, etc.) and generally indicate that the sampling assemblies (e.g., sampling assembly 620 shown in FIG. 11, etc.) can provide accurate results in an urban setting.

In-planta analysis techniques disclosed herein, including in the foregoing examples, may provide quicker results, for example, as compared to sampling tree cores which may require large equilibrium time following sample collection. As previously stated, in-planta analysis techniques disclosed herein may provide samples in about 75 minutes. Thus, less time may be lost waiting for tree core samples to equilibrate. In addition, using in-field analysis and different fibers may allow results to be obtained in minutes (as compared to days if samples are sent to a laboratory for analysis, etc.). In-planta analysis techniques disclosed herein may also provide more accurate results, for example, as compared to sampling tree cores which may become diluted following sample preparation because lower detection limits can be achieved. This may also allow for detection of less volatile contaminants. In addition, multiple samples can be collected in a given day (e.g., one-hundred eighty samples per day, etc.) such that a larger sampling may be obtained at a test site, possibly providing more detailed results.

In other example embodiments, sampling assemblies may include one or more liquid filled components for use in sampling non-volatile compounds (such that the non-volatile compounds may partition to the liquid components for subsequent processing). For example, sampling assemblies may include hollow fiber-liquid filled microextraction (HF-LPME) materials that can be used to provide detection for non-volatile compounds such as, for example, herbicides, nitroaromatics/explosives, other semi-water soluble compounds, etc. These compounds may be more amenable to subsequent processing using liquid chromatography than gas chromatography. Thus, use of, for example, HF-LPME materials in connection with sampling assemblies can allow direct sample collection and analysis with no preparation or phase change (i.e. extraction) steps.

In still other example embodiments, sampling assemblies may include colorimetric indicators configured to indicate presence and/or concentration levels of contaminants present in structures (e.g., plants, buildings, other environmental media, etc.) at a test site.

In other example embodiments, detection of contaminants in vegetation near buildings may be used to indicate contaminant intrusion into a building in question. In-planta analysis techniques as disclosed herein may be used to detect the contaminants.

Various example embodiments are disclosed herein of sampling operations and sampling assemblies used in connection with obtained samples from trees. However, it should be appreciated that the various example sampling operations and sampling assemblies disclosed herein may also be used in connection with obtaining samples from structures other than trees within the scope of the present disclosure, for example plants other than trees, buildings, other environmental media, etc.

In still other example embodiments, sampling assemblies may be configured to be inserted into structures without requiring openings. For example, the sampling assemblies may be equipped with boring devices that allow the sampling assemblies to be generally drilled into a desired structure and left for sampling operation.

Specific dimensions included in the drawings and/or disclosed herein are exemplary in nature and do not limit the scope of the present disclosure.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method for determining the presence of at least one contaminant in a plant, such as a tree, or in a building or in other environmental media located at a test site, the method comprising:
   inserting a sampling assembly into an opening of a plant, building or other environmental media at a test site such that an adsorptive/absorptive portion of the sampling assembly is disposed at least partly in the opening without contacting an inner portion of the plant, building or other environmental media;
   collecting at least one contaminant in the plant, building or other environmental media using the adsorptive/absorptive portion of the sampling assembly; and
   processing at least part of the adsorptive/absorptive portion of the sampling assembly to determine if a contaminant is present in the plant, building or other environmental media.

2. The method of claim 1, further comprising correlating presence of a contaminant in the plant, building or other environmental media to presence of the contaminant in a subsurface below the plant, building or other environmental media.

3. The method of claim 1, further comprising:
   inserting sampling assemblies into openings of multiple plants at the test site such that adsorptive/absorptive portions of the sampling assemblies are disposed at least partly in the openings of the plants without contacting inner portions of the plants;
   collecting at least one contaminant in the plants using the adsorptive/absorptive portions of the sampling assemblies;
   processing at least part of each adsorptive/absorptive portion of each sampling assembly to determine if a contaminant is present in the plant within which the sampling assembly was inserted; and
   correlating presence of contaminants in at least one of the multiple plants to presence of the contaminant in a subsurface below said at least one of the multiple plants.

4. The method of claim 3, further comprising delineating a plume of the contaminant in the subsurface at the test site.

5. The method of claim 3, further comprising assessing a risk associated with vapor intrusion of the contaminant into an interior area located at the test site.

6. The method of claim 1, further comprising creating the opening in the plant, building or other environmental media and inserting the sampling assembly into the opening.

7. The method of claim 1, further comprising sealing at least part of the adsorptive/absorptive portion of the sampling assembly in the opening to inhibit mass transfer through the opening between the plant, building or other environmental media and the surrounding atmosphere.

8. The method of claim 1, wherein the sampling assembly includes a solid phase microextraction sampling device and a support, and wherein inserting a sampling assembly into an opening of a plant, building or other environmental media at a test site includes inserting the support into the opening of the plant, building or other environmental media and inserting at least part of the solid phase microextraction sampling device into a channel extending through the support.

9. The method of claim 1, wherein the sampling assembly includes a solid phase microextraction sampling device and a support, and wherein inserting a sampling assembly into an opening of a plant, building or other environmental media at a test site includes inserting the support into the opening of the plant, building or other environmental media and then inserting at least part of the solid phase microextraction sampling device into a channel extending through the support.

10. The method of claim 1, wherein the adsorptive/absorptive portion of the sampling assembly includes tubing, and wherein collecting at least one contaminant in the plant, building or other environmental media using the adsorptive/absorptive portion of the sampling assembly includes collecting at least one contaminant located within the plant, building or other environmental media using the tubing of the sampling assembly.

11. The method of claim 1, further comprising processing at least part of the adsorptive/absorptive portion of the sampling assembly to determine a concentration of a contaminant present in the plant, building or other environmental media.

12. The method of claim 1, wherein inserting a sampling assembly into an opening of a plant, building or other environmental media at a test site includes inserting the sampling assembly into a tree at the test site; and wherein processing at least part of the adsorptive/absorptive portion of the sampling assembly includes processing at least part of the adsorptive/absorptive portion of the sampling assembly to determine if a contaminant is present in the tree.

13. A method for determining the presence of at least one environmental contaminant in a subsurface of a test site, the method comprising:
   creating an opening in at least one plant, building or other environmental media at a test site;
   inserting a sorption-based sampling device into the opening of the at least one plant, building or other environmental media such that an adsorptive/absorptive portion of the sampling device is disposed at least partly in the opening without contacting an inner portion of the at least one plant, building or other environmental media;
   processing at least part of the sampling device to determine if an environmental contaminant is present in the at least one plant, building or other environmental media in which the sampling device is inserted; and
   correlating an environmental contaminant present in the at least one plant, building or other environmental media to a subsurface below said at least one plant, building or other environmental media, wherein presence of the environmental contaminant in said at least one plant, building or other environmental media is indicative of presence of the environmental contaminant in the subsurface below said at least one plant, building or other environmental media.

14. The method of claim 13, further comprising delineating a plume of the environmental contaminant in the subsurface at the test site.

15. The method of claim 13, further comprising assessing a risk associated with vapor intrusion of the environmental contaminant into an interior area located at the test site.

16. The method of claim 13, further comprising inserting a support into the opening created in the at least one plant, building or other environmental media; and wherein inserting a sorption-based sampling device into the opening created in the at least one plant, building or other environmental media includes inserting the sorption-based sampling device into a channel extending through the support.

17. The method of claim 13, further comprising inserting a support into the opening created in the at least one plant, building or other environmental media; and wherein inserting a sorption-based sampling device into the opening created in the at least one plant, building or other environmental media includes inserting the sorption-based sampling device into a channel extending through the support after inserting the support into the opening.

18. The method of claim 13, further comprising positioning tubing at least partly around a body of each sorption-based sampling device; and wherein inserting a sorption-based sampling device into the opening created in the at least one plant, building or other environmental media includes inserting a body and tubing of a sorption-based sampling device into the opening such that at least part of the tubing is disposed in the opening without contacting an inner portion of the at least one plant, building or other environmental media.

* * * * *